United States Patent [19]

Budd

[11] Patent Number: 4,977,889
[45] Date of Patent: Dec. 18, 1990

[54] FITTING AND TUNING CHEST COMPRESSION DEVICE

[75] Inventor: Jeffrey R. Budd, St. Paul, Minn.

[73] Assignee: Regents of the University of Minnesota, Minneapolis, Minn.

[21] Appl. No.: 420,276

[22] Filed: Oct. 12, 1989

[51] Int. Cl.$^5$ ............................................. A61H 31/02
[52] U.S. Cl. ................................. 128/30.2; 128/24 R; 128/30
[58] Field of Search ...................... 128/24 R, 25 R, 30, 128/30.2, 39, 40, DIG. 20, 202.16, DIG. 13; 272/130, DIG. 5

[56] References Cited

U.S. PATENT DOCUMENTS

| | | | |
|---|---|---|---|
| 2,918,917 | 12/1959 | Emerson | 128/39 X |
| 3,802,417 | 4/1974 | Long | 128/30.2 X |
| 4,296,743 | 10/1981 | Lasley | 128/30 |
| 4,464,172 | 8/1984 | Lichtenstein | 128/DIG. 13 X |
| 4,621,621 | 11/1986 | Marsalis | 128/202.12 X |
| 4,676,232 | 6/1987 | Olsson et al. | 128/30.2 X |
| 4,838,263 | 6/1989 | Warwick et al. | |

OTHER PUBLICATIONS

Zamir Hayek, M.D., "External High Frequency Oscillation-A New Concept in Ventilation", pp. 1–16, Jul. 8, 1989, Tokyo, Japan.
Monica Gutierrez et al., "Weekly Cuirass Ventilation Improves Blood Gases and Inspiratory Muscle Strength in Patient with Chronic Air-Flow Limitation and Hypercarbia", pp. 617–623, American Review of Respiratory Disease, vol. 138, 1988.
Nicholas S. Hill, M.D., F.C.C.P., "Today's Practice of Cardiopulmonary Medicine-Clinical Applications of Body Ventilators", pp. 897–905, Chest, vol. 90, No. 6, 1986.
Jacques Piquet et al., "High Frequency Transthoracic Ventilation Improves Gas Exchange During Experimental Bronchoconstruction in Rabbits", pp. 605–608, American Review of Respiratory Disease, vol. 133, 1986.
Zamir Hayek et al., "External High Frequency Oscillation in Cats", pp. 630–634, American Review of Respiratory Disease, vol. 133, 1986.
M. King et al., "Enhanced Tracheal Mucus Clearance with High Frequency Chest Wall Compression", pp. 511–515, American Review of Respiratory Disease, vol. 128, 1983.
P. E. Krumpe et al., "Comparison of the Effects of Continuous Negative External Chest Pressure and Positive End-Expiratory Pressure on Cardiac Index in Dogs", pp. 39–45, American Review of Respiratory Disease, vol. 128, 1983.
Commercial Brochure entitled "The Hayek Oscillator", Published by Flexco Medical Instruments, Kirchweg 151, 8102 Oberengstringen, Zurich, Switzerland.

Primary Examiner—Richard J. Apley
Assistant Examiner—Linda C. Maas Dvorak
Attorney, Agent, or Firm—Merchant, Gould, Smith, Edell, Welter & Schmidt

[57] ABSTRACT

Persons having respiratory diseases often have treatment programs including a pummeling of the thoracic cavity for the purpose of aiding respiration. A vest as a part of an alternating compression machine is used to eliminate the need for trained physical therapists and rather provide for mechanical thumping. A fitting routine for the vest is provided. A routine for identifying optimal operating frequencies for the machine is also provided, along with an algorithm for selecting appropriate frequencies.

9 Claims, 10 Drawing Sheets

Example Ordering Of Frequencies

| Frequency | Peak Flow Rank | Compression Volume Rank |
|---|---|---|
| 6 | 17 | 5 |
| 7 | 16 | 6 |
| 8 | 10 | (1) |
| 9 | 5 | 3 |
| 10 | 6 | (2) |
| 11 | (2) | 4 |
| 12 | 4 | 7 |
| 13 | 3 | 10 |
| 14 | (1) | 8 |
| 15 | • | • |
| 16 | • | • |
| 17 | • | • |

FIG. 18

Example Ranking

| Frequency | Averaged Ranking | |
|---|---|---|
| 6 | 22.17 | |
| 7 | 22.16 | |
| 8 | 11.10 | — Already Chosen |
| 9 | (8.05) | |
| 10 | 8.06 | — Already Chosen |
| 11 | 6.04 | — Already Chosen |
| 12 | (11.07) | |
| 13 | 13.10 | |
| 14 | 9.08 | — Already Chosen |
| 15 | • | |
| 16 | • | |
| 17 | • | |

FITTING AND TUNING CHEST COMPRESSION DEVICE

FIELD OF THE INVENTION

The present invention is directed to a medical device and procedure and, more particularly, to the fitting and frequency tuning of an alternating chest compression device useful for loosening and helping to eliminate mucous from the lungs of people afflicted with respiratory diseases, for example, cystic fibrosis.

BACKGROUND OF THE INVENTION

The chest compression apparatus first disclosed in U.S. Pat. No. 4,838,263 was developed to help people with cystic fibrosis. Conventional treatment for the disease involved an aerosol therapy three or four times a day to obtain bronchial drainage and a daily physical pounding on the chest wall to loosen mucous for expectoration. Daily treatment could range from four to six hours plus and necessitated a respiratory therapist or at least a trained individual to provide the pummeling of the chest. The chest compression apparatus provided an alternative for pounding the chest wall and loosening the mucous for expectoration. The alternative was especially significant since it gave the patient much greater flexibility with respect to treatment schedule, reduced cost of treatment, and increased psychological and physical freedom and self-esteem.

As research and development continued, it has become evident that the chest compression apparatus can be optimized with respect to aiding respiration. The present invention is directed to an apparatus and method for optimizing the fit of the vest or other compressing mechanism which surrounds the thoracic cavity and for optimizing the frequencies of alternating compression which are most effective for a particular patient.

SUMMARY OF THE INVENTION

The alternating compression device for the thoracic cavity of a person includes a mechanism for compressing the person's thoracic cavity and mechanism for providing an alternating pressure to the compressing mechanism. The compressing mechanism is adjustable with respect to the thoracic cavity. The apparatus of the present invention is directed to optimizing the fit of the compressing mechanism and identifying frequencies at which the device functions most beneficially for a particular person. The invention includes mechanism for measuring actual air flow from the person during respiration while the alternating compression device is operating. The invention also includes mechanism for computing from the measured actual air flow the parameters of normal air flow of the person as if the alternating compression device were not operating, normal lung volume of the person as if the alternating compression device were not operating, induced air flow peaks relative to the normal air flow and due to the alternating compression device operating, average of the induced air flow peaks, and average of the induced changes in lung volume relative to the normal lung volume and due to the alternating compression device operating. The invention further includes mechanism for connecting the air flow measuring mechanism and the computing mechanism such that measured air flow is converted to electrical signals compatible with the computing mechanism. In this way, the fit of the compressing mechanism is optimized when the induced air flow peaks are substantially the same relative to normal lung volume during respiration. Optimal frequencies for a particular person occur when average induced air flow peaks and average induced lung volume changes are greatest.

The method for using the invention includes installing the compressing mechanism on the person, measuring observed air flow at the mouth of the person during respiration to determine the efficacy of the compressing mechanism, and identifying frequencies which are optimal for enhancing the person's respiration.

It has been found that compressing mechanisms, such as vests, can be too loose or too tight and, consequently, reduce the effectiveness of the chest compression device with respect to a particular person. The present invention provides a way to know when the fit of the vest is proper. Furthermore, the present invention provides a way to select frequencies for a properly fitted vest which result both in the most efficient thumping of the thoracic cavity for the purpose of loosening mucous and also for the most efficient air flow which results in expectoration. Consequently, the present invention significantly enhances the effectiveness of the treatment of patients who can benefit from an alternating chest compression device.

BRIEF DESCRIPTION OF THE DRAWINGS

The structure and advantages of the present invention are explained with particularity hereinafter by referring to the drawings briefly described as follows.

DETAILED DESCRIPTION OF THE PREFERRED EMBODIMENT

Figure 1:
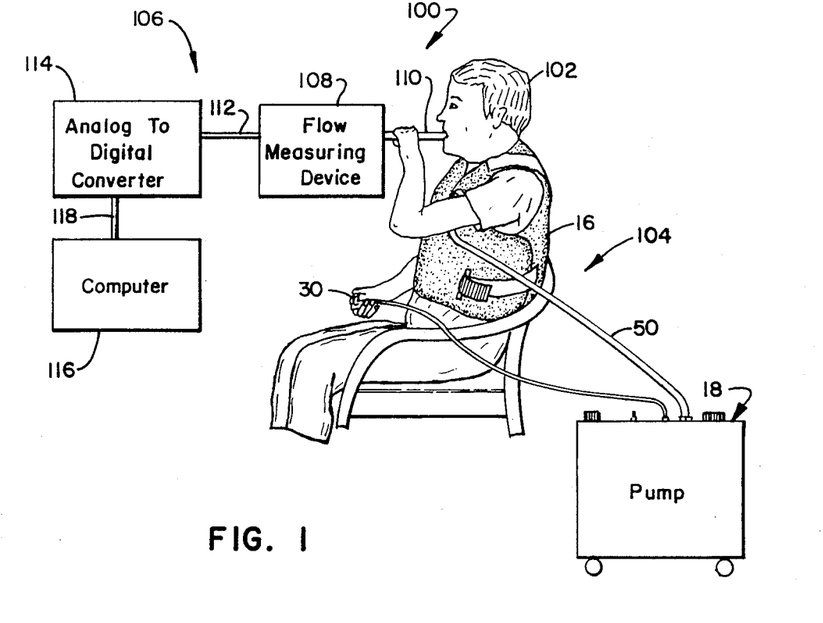
FIG. 1 is an illustration of a person operating an apparatus useful for optimizing fit and operating frequency of an alternating chest compression device in accordance with the present invention.

Referring then to the drawings wherein like reference numerals designate identical or corresponding parts throughout the several views, and more particularly to FIG. 1, an apparatus in accordance with the present invention is illustrated and is designated generally by the numeral 100. Person 102 is shown operably engaged with alternating chest compression device 104 and is illustrated to be operably engaged with mechanism 106 useful for optimizing device 104 in accordance with the present invention. Device 104 includes an air vest or bladder 16 constructed to apply a fairly uniform pressure to the thoracic cavity region of person 102. A hose 50 connects an air pulse pumping system 18 with vest 16. Person 102 is shown holding a switch 30 which controls the pressurizing of vest 16 as described more fully hereinafter.

Before describing compression device 104 more fully, however, note that optimizing mechanism 106 includes a flow measuring device 108 in fluid communication with usually the mouth of person 102 via a conduit 110. Flow measuring device 108 provides electrical signals via line 112 to an analog-to-digital converter 114 which accesses a computer 116 via line 118.

An appropriate flow measuring device is available from Vacumed, Inc., 2261 Palma Drive, Ventura, California 93003. The device includes a mouthpiece (catalog no. 1002) for connection with a clinical pneumotachometer (catalog no. R4700). The pneumotachometer is connected to a differential pressure transducer (catalog no. 4500-2) which provides an electrical signal to a carrier demodulator (catalog no. 4510). An analog-to-digital converter suitable to be used with the indicated items and also suitable with respect to the computer mentioned hereinafter may be obtained from Scientific Solutions, Inc., 6225 Cochran Road, Solon, Ohio 44139 under the name Lab Master (catalog no. 20009). A suitable computer is Turbo XT-IBM XT compatible (catalog no. 63060) available from CompuAdd Corporation, 12303 Technology Boulevard, Austin, Texas 78727.

Figure 2:
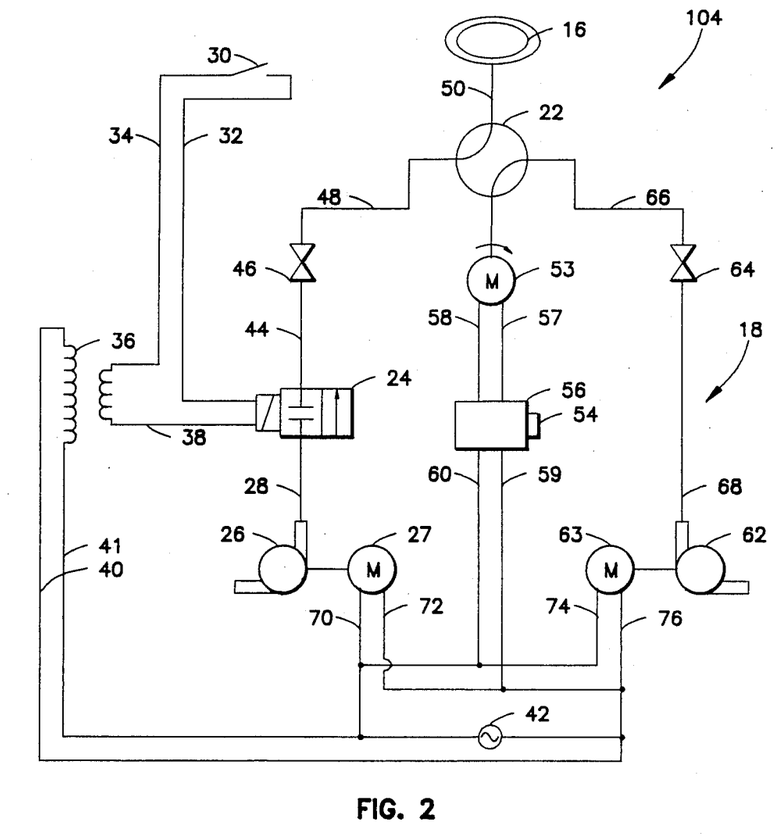
FIG. 2 is a schematic diagram of a chest compression device of the type in accordance with the present invention.

Compression device 104 is described in detail in U.S. Pat. No. 4,838,263, hereby incorporated by reference. As shown in FIG. 2, the air pulse system 18 of apparatus 104 comprises a pair of high volume regenerative blowers 26 and 62 having output which is controlled by a large bore rotary valve 22. The pressure side blower 26 has been tested using a commercially available unit capable of producing a pressure of 43 inches of water at a volume of 53 cubic feet per minute. Blower 26 is driven by a motor 27. The test unit was driven by a one-half horsepower AC motor at 1725 rpm. The evacuation side blower 62 is driven by a motor 63. The test blower was capable of producing a pressure of 28.5 inches water at a volume capacity of 27 cubic feet per minute. The test blower was operated by a one-eighth horsepower AC motor at 1725 rpm. Preferably, the pressure side blower 26 is oversized relative to the evacuation side blower 62, as indicated with respect to the test units to accomplish fast reinflation of vest bladder 16 after it has been evacuated.

Alternate positive and negative pressures are applied to vest 16 via a rotary valve 22. During the positive input pulse through valve 22 the negative pressure side of the system is closed. During the negative pressure pulse the positive pressure side of the system is closed. The rotary valve creates alternating positive and negative pressure pulses to vest 16 and is driven by motor 53. During testing, a one-twentieth horsepower DC motor 53 controlled by a conventional DC controller 54 was used. An electronic tachometer with a magnetic pickup was used to monitor valve rotational speed. The blowers operated continuously, so that pulse speed was regulated by controller 54.

A solenoid valve 24 is located between the positive side blower 26 and the rotary valve 22. During testing, solenoid valve 24 had a 1.25 inch bore and was operated by 24 volt power. Valve 24 is normally closed and is controlled by a patient held hand switch 30. In the open position a positive 43 inches of water pressurized air flow is applied to rotary valve 22 which in turn allows the air in the form of a pressure pulse through to vest bladder 15. Since rotary valve 22 opens and closes air flow between positive side blower 26 and vest bladder 16, pulses are created. The pulsing rate is determined by the rotational speed of rotary valve 22 which in turn is determined by motor controller 54.

When solenoid valve 24 is in the closed position, no air flow from the positive side blower 26 passes to vest bladder 16. Rather, vest bladder 16 is evacuated by negative pressure side blower 62. Such evacuation reduces the efforts required by a patient during inhalation. Some patients may find a negative pressure is not needed to evacuate the vest for comfortable inhalation. For such patients, the vacuum or negative pressure blower 62 is optional.

A manual flow valve 46 is located between positive pressure blower 26 and vest bladder 16 to provide adjustment for regulating the flow volume or pulse strength to vest 16. Likewise, a manual flow valve 64 is located between rotary valve 22 and negative side door 62 to provide control relating to evacuation. That is, for some patients total evacuation of vest bladder 16 may be unnecessary or undesirable. Since rotary valve 22 rotates at a constant speed and since negative side blower 62 operates at a constant speed, when flow valve 64 is set to constrict the flow communication line between rotary valve 22 and blower 62, it will in effect reduce the volume of air which is evacuated during a revolution of rotary valve 22. Therefore, depending on how long the pressure side of apparatus 10 is closed, complete evacuation by the evacuation side may not occur.

With reference to FIG. 2, apparatus 10 is hereinafter described even more particularly. Pressure side blower 26 is in flow communication through hose 28 with normally closed, solenoid valve 24. It is understood that any reference to a hose could as well be a pipe or other mechanism for directing air from one point to another. Solenoid valve 24 is in flow communication with rotary valve 22 through a flow control valve 46, preferably manually operable, wherein hose 44 connects solenoid valve 24 with flow control valve 46 and hose 48 connects flow control valve 46 with rotary valve 22. One or more lines shown as hose 50 connect rotary valve 22 with vest 16. On the negative pressure side, rotary valve 22 is in flow communication through flow control valve 64 with evacuation fan 62. Hose 66 connects rotary valve 22 with flow control valve 64, while hose 68 connects valve 64 with fan 62.

AC motor 27 drives pressurizing fan 26 and is connected via electrical lines 70 and 72 to electrical power source 42. AC motor 63 drives evacuation fan 62 and is connected via lines 74 and 76 to power source 42. DC motor 53 is connected via lines 57 and 58 with controller 54. Controller 54 includes a manual control 56 for varying speed of motor 53. Motor controller 54 receives power via lines 59 and 60 from source 42.

Solenoid valve 24 is connected through an isolation transformer 36 to power source 42. More particularly, solenoid valve 24 is connected to one side of transformer 36 via line 38 and to the other side of transformer 36 via lines 32 and 34 through patient control switch 30. The other side of transformer 36 is connected to power source 42 via lines 40 and 41.

A cystic fibrosis patient is generally weak and has a weak cough and cannot clear mucus from his/her lungs, sometimes hardly at all. A high frequency vibration aids in decreasing the viscosity of the mucus, freeing it from lung walls and thus making it much more likely that a weak cough will be able to clear mucus. As some mucus is cleared, the cough will likely strengthen thereby allowing more and more mucus to be cleared.

Figure 3:
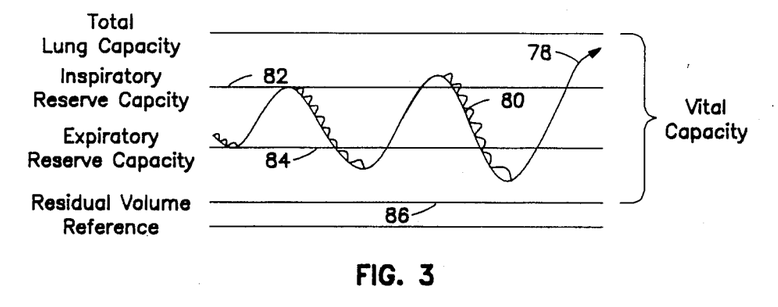
FIG. 3 is an illustration of pressure pulses superimposed on an oscillatory curve representing a person's breathing cycle.

A more graphic representation is shown in FIG. 3. The lower frequency line 78 represents the air flow during a normal breathing cycle of the patient. The higher frequency line superimposed on portions of the low frequency line represents the induced air flow due to the vest 16 about the patient's thoracic cavity.

Initially, the patient breathes rather shallow and uses only a small percentage of his/her total lung capacity as represented by the region between the inspiratory reserve capacity line 82 and the expiratory reserve capacity line 84. As some mucus clears, the patient begins using a greater percentage of his/her lung capacity. A treatment goal is to get the patient breathing so deeply that he/she reduced his/her residual volume as represented by line 86, thereby increasing his/her vital capacity.

The vest typically has a single air chamber with at least one and preferably two air ports located near the upper portion of the chest. The vest, on a test model, was made of 15 mil polyurethane with hook and loop closures in front. To use, after the patient has been fitted with a vest 16 such that the vest conforms to the patient's chest snugly, but not tightly, hose 50 is connected thereto. The three motors 27, 53 and 63 are then turned on. Since solenoid valve 24 is normally closed, fan 26, although now operating, is not yet pressurizing vest bladder 16. Evacuation fan 62, also now operating, is functioning to evacuate vest bladder 16. The patient then closes switch 30 which opens solenoid valve 24 and allows for pressurization of vest bladder 16 and does so with air pulses at a frequency set by control 56 of motor controller 54. If the volume of air from either the pressure side or the evacuation side of the system is too great or not enough, hand control valves 46 and 64 are appropriately functioned.

With the system operating, the patient must learn to control apparatus 10 in accordance with his/her breathing cycle. That is, switch 30 must be held down during expiration and released during inspiration so as to provide pulsing during expiration and evacuation during inspiration. The effect is shown graphically in FIG. 3 by the smooth line 78 directed toward inspiratory reserve capacity line 82 and the superimposed wavy line 80 on line 78 directed toward expiratory reserve capacity line 84. For many situations, the pulsing may be applied during both inspiration and expiration. The high frequency pulse rate appropriate for any particular patient is obtained by empirically measuring the flow rate breathed by the patient at different frequencies and at different time durations of the treatment with apparatus 10. The present apparatus is particularly advantageous in this regard since the pulsing frequency can be tuned to a particular patient to optimize energy transmission to the lungs. Typically, the breathing cycle is a relatively low frequency and for a healthy person is commonly about .2 to .4 hertz. For a person having cystic fibrosis or other sickness, the breathing frequency may range up to one or two hertz. The high frequency pulsing is generally tuned between 10 to 30 hertz and could go as high as the 30 hertz rate for a small child. In any case, the low frequency breathing cycle will be below 5 hertz, while the high frequency pulsing cycle will be above 5 hertz.

It is noted then that the preferred embodiment apparatus provides a patient a number of advantageous features. Compression pulsing is applied to the entire thoracic cavity. Pulsing frequency may be tuned for optimal energy transmission. Apparatus 10 is patient controlled. If the patient drops switch 30, apparatus 10 simply evacuates pressure.

Figure 4:
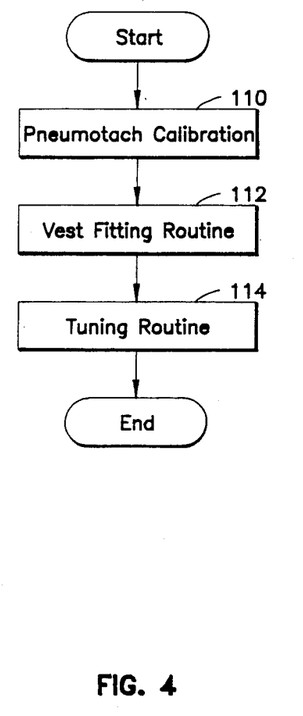
FIG. 4 is a block diagram of the method of the present invention.

The method for using the optimizing mechanism 106 to properly fit vest 16 of compression device 104 and to obtain operating frequencies is shown in general terms by the block diagram of FIG. 4. The method begins by calibrating the pneumotach as indicated by box 110. The calibration is followed by a vest fitting routine 112 which is followed by a frequency tuning routine 114.

The calibration procedure is conventional and well known to those skilled in the art. Briefly, the calibration process is based on the standard practice used in pulmonary function testing. First, the voltage signal from the flow device is sampled during zero flow. The average of the value sampled during this short time period is subtracted from all values subsequently sampled to get flow relative to zero flow. Next, three injections and withdrawals of air are performed with a three litre calibration syringe. An appropriate syringe (catalog no. R5530) is available from Vacumed, Inc. By sampling the flow signal during this maneuver, the three inspiratory and expiratory volumes can be computed by adding the digitized flow values and dividing by the sample rate. By averaging the three volumes and comparing to the desired three litre volume a scale factor is computed for both inspiratory and expiratory flow. These scale factors, along with the zero flow average, are used in all subsequent calculations of flow and volume.

Following calibration, the vest is fitted. Essentially, the patient is told to breath through the flow device with the vest on and the compression device 104 operating at a mid-range frequency, for example, 14 hertz. The specific maneuver to be followed is a maximum inspiration followed by a maximum expiration. What is seen is a sinusoidal flow signal generated at 14 hertz by the vest which is superimposed on the maximum breathing maneuver of the patient. By filtering out the 14 hertz signal, the underlying patient generated signal is exposed. By exposing the underlying patient generated signal, lung volume can be computed for all points during the maneuver by integrating the flow signal. By subtracting the patient signal from the observed air flow signal, the induced signal generated by the vest is exposed. The maximum induced air flow peaks can be identified and plotted against lung volume. A well fitting vest has similar values across all lung volumes. A vest that is too loose will not have enough compression at low lung volumes, while a vest that is too tight will be so restrictive at high lung volumes that vest induced air flow will fall off at those points. In order to discriminate between two different vests which have approximately even distributions of the induced peak air flow measure, the relative values of the peak air flow values are reviewed and the vest having the highest values is chosen.

Figure 5:
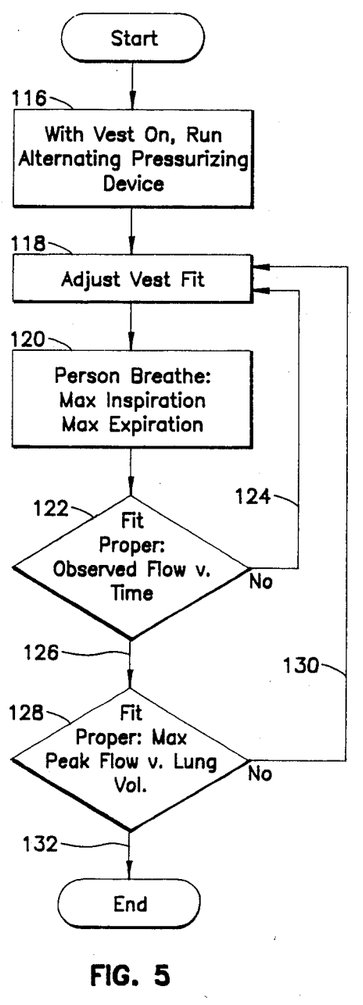
FIG. 5 is a block diagram of the vest fitting routine step of FIG. 4.

With reference to FIG. 5, the fitting routine begins by installing the vest on the person and running the device 104 as shown in box 116. As shown in box 118, the vest is then adjusted so that as pressure pulses are applied, the vest is not too loose and not too tight. As indicated in box 120, the person then makes a deliberate maximum inspiration following by a maximum expiration. The flow from a complete maximum expiration is shown by curve 123 in FIG. 6. As indicated by box 122, an initial determination with respect to proper fit can be made from curve 123. Curve 123 is a plot of observed or measured air flow from the person as a function of time. Curve 123 shows that the vest fit is loose in that as air is expired from the lungs, the effect of the pressure pulses due to the vest becomes less and less. The objective is to have a relatively constant effect throughout a respiration cycle.

Figure 6:
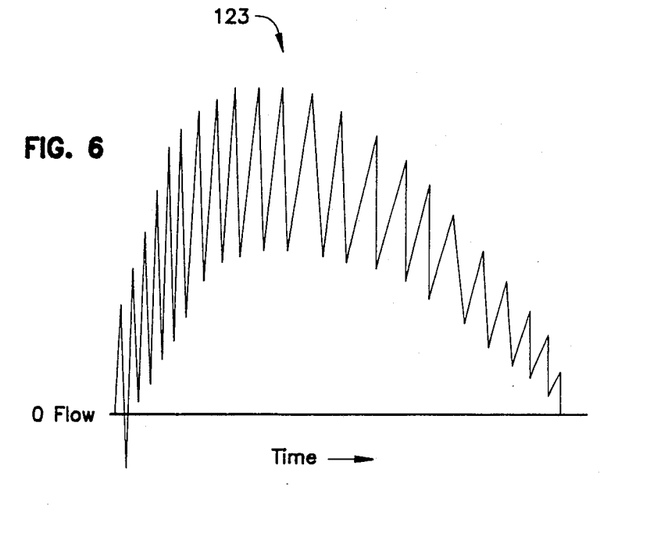
FIG. 6 is a graph of measured air flow of an expiratory maneuver of a person wearing a loose compression mechanism.
Figure 7:
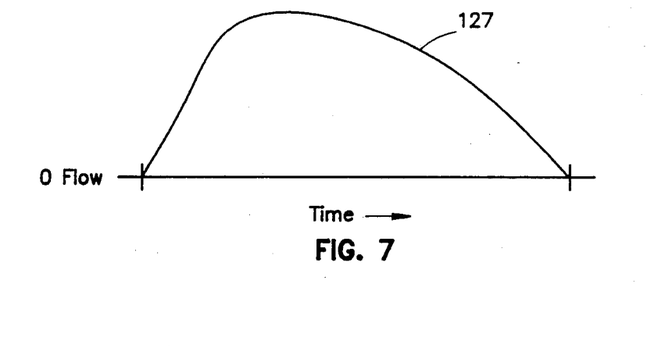
FIG. 7 is a graph similar to FIG. 6 except the induced air flow oscillations have been filtered out.
Figure 8:
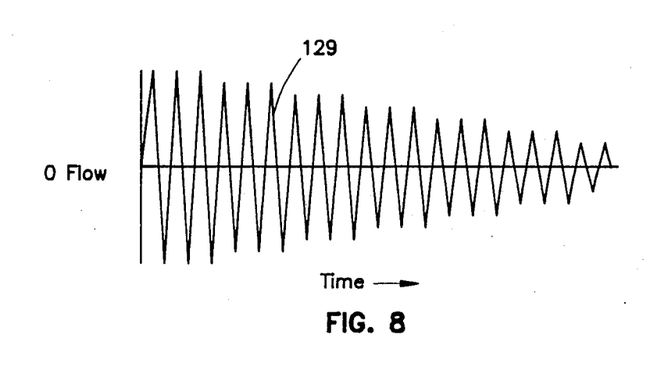
FIG. 8 is a graph similar to FIG. 6 except the patient flow of FIG. 7 has been subtracted.
Figure 9:
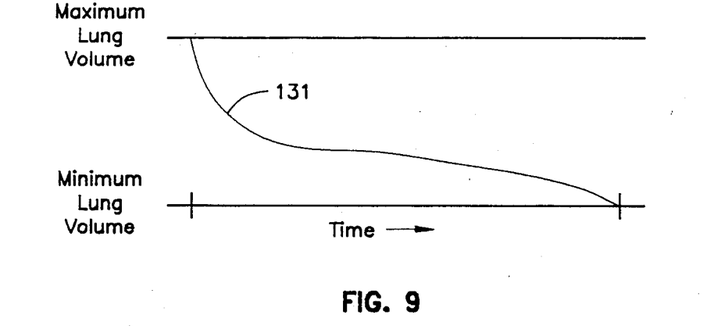
FIG. 9 is a graph of the curve of FIG. 7 integrated over time to show the person's lung volume.
Figure 10:
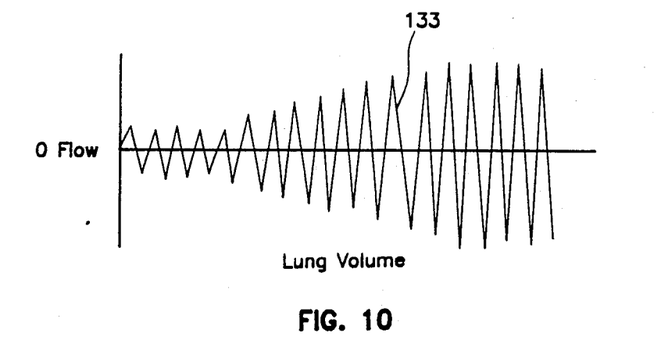
FIG. 10 is a graph of induced air flow versus lung volume.
Figure 11:
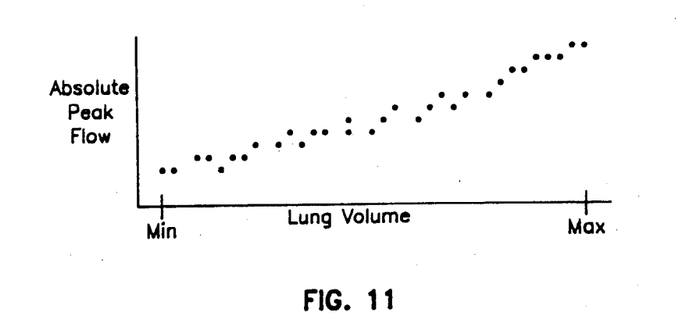
FIGS. 11 and 12 are graphs of absolute peak air flow versus lung volume.
Figure 12:
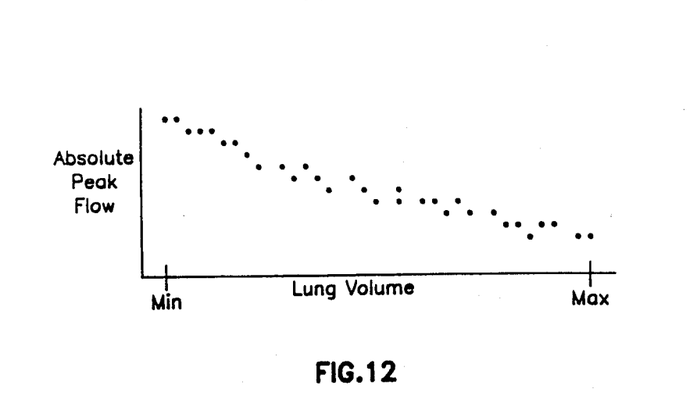

As indicated by line 124, if the fit is improper, the next step is to return to box 118 and adjust the vest. The maximum inspiration and expiration maneuver is performed again and another curve like that of FIG. 6 is reviewed. When the vest has been fitted relatively good so that the pressure pulses seem to have an approximately constant effect throughout the breathing cycle, then as indicated by line 126 leading to box 128, a more sophisticated determination of fit is made by considering the relationship of maximum induced peak flow absolute values versus lung volume. The indicated relationship is obtained by filtering the induced air flow due to the pressure pulses applied by the vest from normal patient air flow so that curve 123 of FIG. 6 becomes curve 127 of FIG. 7. The values represented by patient flow curve 127 can then be subtracted from curve 123 to obtain induced air flow as a function of time depicted by curve 129 in FIG. 8. Curve 131 of FIG. 9 shows lung volume as a function of time and is obtained by integrating over intervals of time, curve 127 of FIG. 7. The air flow values of FIG. 8 can then be plotted with respect to lung volume values of FIG. 9 to obtain an appropriate induced flow versus lung volume curve 133 as shown in FIG. 10. It is noted that lung volume has minimum values at the left and maximum values at the right. Next, the peak air flow absolute values greater than and less than zero induced flow are identified and plotted relative to lung volume as shown in FIGS. 11 and 12. If the slope of the plot is positive, the vest is still too loose. If the slope is negative as shown in FIG. 12, the vest is too tight. In either case, as shown by line 130 in FIG. 5, the next step would be to further adjust the vest and repeat the process. When the vest is finally properly fitted which would be the case if the slope of the plot of a type shown in FIGS. 11 and 12 is essentially zero, then as line 132 indicates, the vest fitting routine would be completed.

Appendix A provides a more detailed disclosure of the vest fitting routine in the form of an annotated computer program.

The tuning routine begins by choosing a frequency sequence protocol. After that, the routine proceeds in a similar fashion to the vest fitting routine. The person, however, breathes through the flow measuring device in a normal breathing pattern. Air flow from the patient is sampled either for a set time period, for example, two seconds, or for a set number of breaths, for example, one or two breath cycles. The first option is much easier since the detection of breath onset and end is often difficult, particularly in view of the fluctuations added by compression device 104. The vest induced air flow signal is filtered from the patient generated air flow signal. The result is then subtracted from the patient generated signal to obtain an induced air flow versus time. The half cycles are integrated to obtain volume and the peaks are identified with both averaged over the selected interval and stored so that the frequencies having the greatest average induced air flow peaks and greatest average induced changes in lung volume can be identified.

Figure 13:
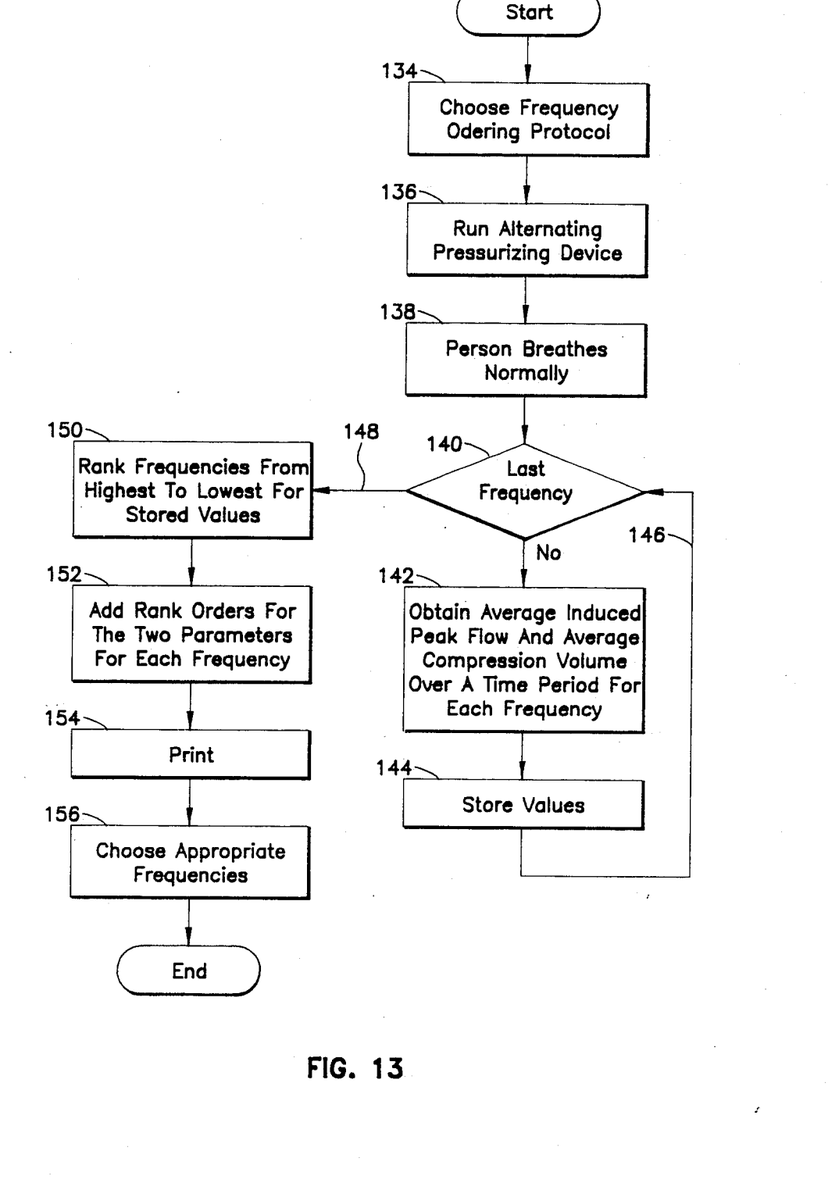
FIG. 13 is a block diagram of the tuning routine step of FIG. 4.

The routine for identifying optimum operating frequencies for compression device 104 is illustrated in FIG. 13. As depicted by box 134, it is necessary first to choose a frequency ordering protocol. That is, frequencies may be applied from smallest to largest or largest to smallest or randomly or by some other scheme. Once the protocol is established, compression device 104 is operated as indicated by box 136. For this routine, the person breathes normally as shown by box 138. In this regard, curve 135 in FIG. 14 substantially depicts a normal breathing cycle, while curve 137 shows induced air flow superimposed thereon for the case of a properly fitting vest.

Assuming the operating frequency of device 104 is not the last frequency to be tested as indicated by box 140, it is necessary to obtain average induced peak air flow and average induced changes in lung volume for a preselected time as indicated by box 142. The values for each frequency are stored as indicated by box 144. And as indicated by line 146, frequencies are changed and the indicated values are obtained until values have been obtained for all frequencies.

Figure 14:
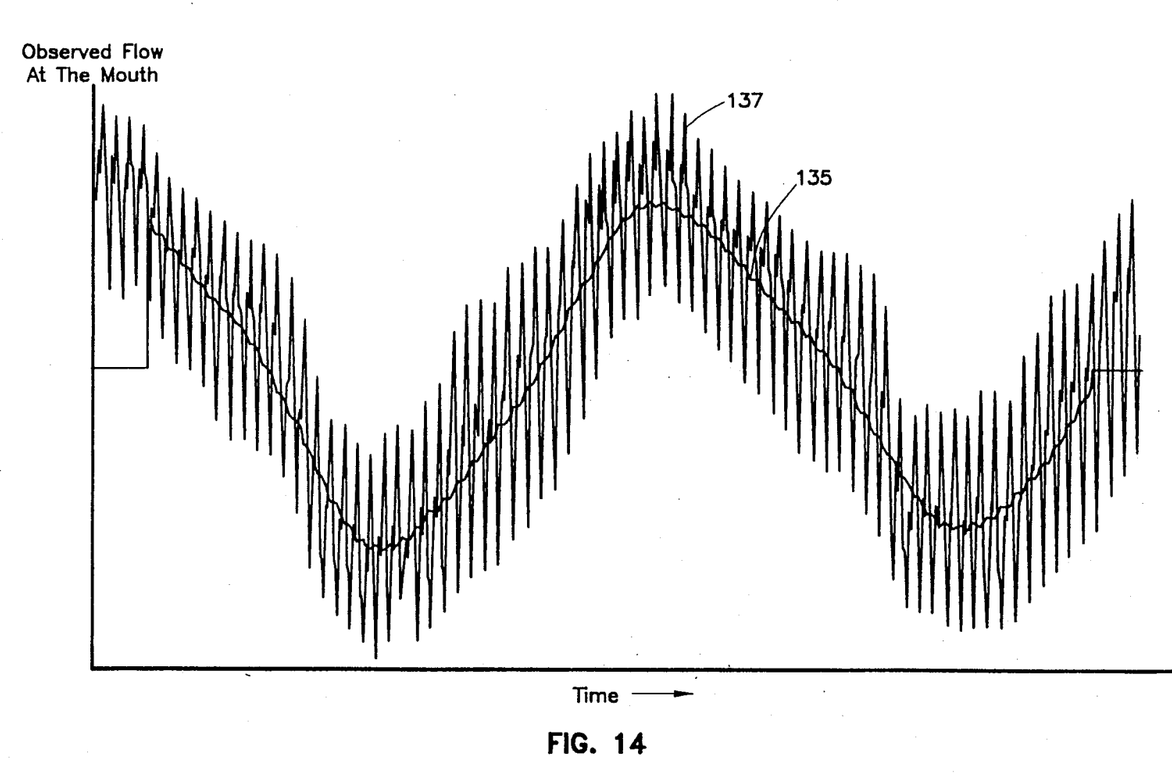
FIG. 14 is a graph of breathing cycle for a person wearing a properly fitting vest.
Figure 15:
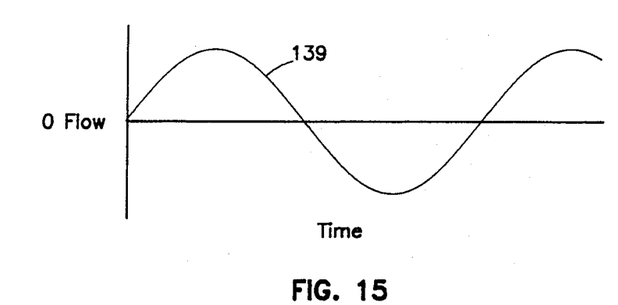
FIG. 15 is a graph similar to FIG. 14 except induced air flow has been filtered out.
Figure 16:
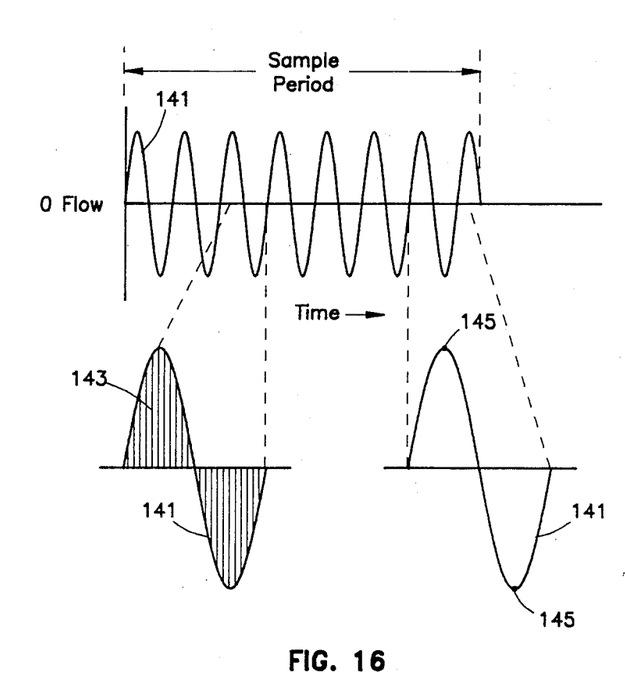
FIG. 16 is a graph of induced air flow versus time, further illustrating induced lung volume and induced peak air flow.

To obtain the averages of the indicated parameters, the induced air flow is filtered from curve 137 shown in FIG. 14 to obtain curve 139 (which is essentially curve 135) as shown in FIG. 15. Curve 139 is then subtracted from curve 137 to obtain an induced air flow curve 141 as shown in FIG. 16. Each half cycle of curve 141 is integrated as shown by the shaded area 143 on the left to obtain induced changes in lung volume. The absolute value of each is taken and an average over the preselected sample period is obtained with the average induced changes in lung volume then stored as indicated by box 144. Also, the induced peak air flow values 145 are identified with respect to curve 141 as indicated by the enlarged cycle on the right and the absolute values are obtained and averaged over the preselected sample period. The average induced peak air flow is then also stored as indicated by box 144. When values have been obtained for all frequencies, the iterative part of the routine is complete and as indicated by line 148, the frequencies are next ranked.

The vest frequency tuning routine described thus far is disclosed in greater detail in Appendix B which provides an annotated computer program.

Figure 17:
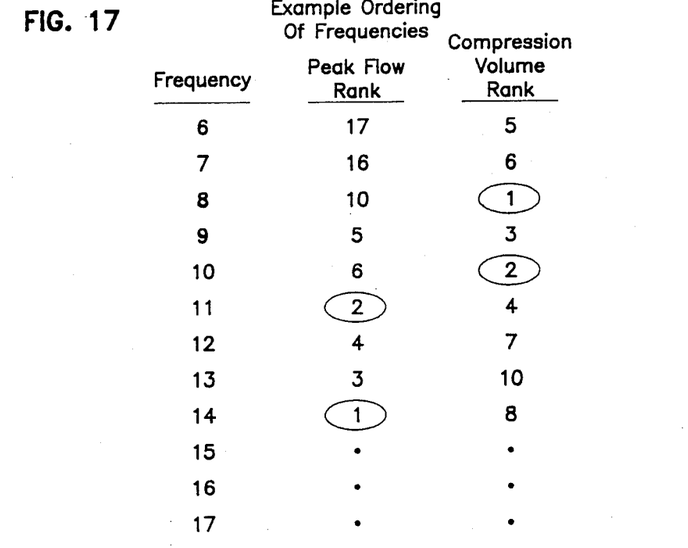
FIG. 17 is a table providing an example of ordering of frequencies based on peak air flow and changes in lung volume; an FIG. 18 is a table of an example reranking of frequencies based on the average ranking of the same frequencies in table 17.

When all the average absolute values of induced peak air flow and of changes in lung volume have been obtained, as indicated by box 150 in FIG. 13, the frequencies are ranked from highest to lowest for both groups of stored values. An exemplary ordering of frequencies is shown in the table of FIG. 17. In that regard, it is noted that the highest average induced peak flow was obtained at 14 hertz with the second highest being 11 hertz. The highest average induced change in lung volume was obtained at 8 hertz with the second being 10 hertz.

In prescribing a treatment program, the concept is to first give the thoracic cavity a good thumping to loosen mucous, then to increase the air volume moved slightly while still retaining some thumping action, and finally supplying good air movement to move the mucous. This is accomplished by selecting frequencies first which create the greatest induced peak air flows, next those which are not the highest for either thumping or air movement, but which have the highest average ranking of the two parameters. Finally, the air movement frequencies are represented by those having the highest values of induced changes in lung volume. The reranking of frequencies according to those having the highest average ranking is indicated by box 152 with an exemplary table shown in FIG. 18. Since 4 frequencies have already been chosen for different reasons, the next two frequencies having the highest average ranking are those at 9 and 12 hertz.

Figure 18:
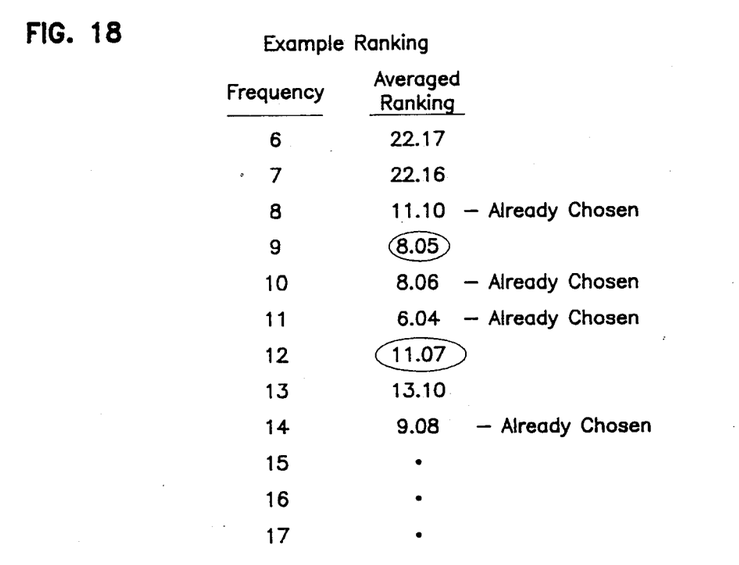

With the frequencies ranked by the computer, as indicated by boxes 154 and 156, the tables represented in FIGS. 17 and 18 are printed and appropriate frequencies chosen as already described. At this point, the tuning routine having the purpose of identifying optimal operating frequencies is complete.

The alternating compression device 104 has been found to be an important advance in treatment programs for persons having respiratory problems, particularly cystic fibrosis. The optimizing mechanism 106 and the method for using it as described herein result in a properly fitting vest 16 and a list of operating frequencies which are optimum for different purposes for a particular patient. The present invention is particularly advantageous in that the efficacy of the vest can be determined by only measuring air flow at the mouth of the person. The vest fitting routine is further significant in that a method has been identified for separating normal air flow of the person from induced air flow for relating to lung volume thereby determining the effects of the vest on lung volume and further determining the fit of the vest based on these parameters. The tuning routine is similarly significant in that the average peak air flow and average change in lung volume for a normal tidal volume maneuver at different frequencies can be obtained and used to identify the best frequencies which achieve chest thumping and which achieve air movement and further those which are good at both results so that a selected treatment program of frequencies can be prescribed.

Thus, the preferred embodiment of apparatus and the method of using it have been described in detail. It must be understood, however, that the disclosure is exemplary and equivalents are possible. Therefore, in this regard, it is understood that changes made, especially in matters of shape, size, and arrangement to the full extent extended by the general meaning of the terms in which the appended claims are expressed, are within the principle of the invention.

APPENDIX A   (VEST FITTING ROUTINE)

```
1005 DIM OBSERVE(2000),PATIENT(2000),VEST(2000)
1010 PRINT "SET FREQUENCY TO 14 HZ"          ** Do analog to digital sampling
1020 TIME=10                                  ** for 10 seconds at 200 Hz and
1030 INPUT "PATIENT READY?";A$                ** put scaled values in OBSERVE
1040 GOSUB 8000
1050 REM - FILTER TO GET PATIENT FLOW         ** Moving average filter OBSERVE
1060 GOSUB 9000                               ** and put results in PATIENT
1070 REM - SEPARATE VEST FLOW & GET VOLUME
1080 VOL=10000                                ** Start at 10000 ml
1090 MAX=-1000000                             ** Initialize variables
1100 MIN=1000000
1110 FOR I=BEGIN TO FINAL
1120    J=I-BEGIN+1                           ** New values start at position 1
1130    VEST(J)=OBSERVE(I)-PATIENT(I)         ** Vest induced flow
1140    VOL=VOL-PATIENT(I)/200                ** Integrate for volume (200 Hz)
1150    PATIENT(J)=VOL                        ** PATIENT now holds lung volume
1160    IF VOL<MAX THEN GOTO 1190
1170       MAX=VOL                            ** New volume maximum
1180       NMAX=J                             ** and its position
1190    IF VOL>MIN THEN GOTO 1220
1200       MIN=VOL                            ** New volume minimum
1210       NMIN=J                             ** and its position
1220 NEXT I
1230 REM - FIND PEAK VEST FLOWS & RELATE TO VOLUME
1240 SIGN=1                                   ** SIGN=1 when positive vest flow
1250 IF VEST(NMAX)<0 THEN SIGN=-1             ** SIGN=-1 when negative
1260 N=0
1270 MAX=0
1280 SUMX=0                                   ** Initialize correlation sums
1290 SUMXX=0
1300 SUMY=0
1310 SUMYY=0
```

```
1320 SUMXY=0
1330 OPEN "GRAPH.PLT" FOR OUTPUT AS #1      ** Open file for later graphing
1340 FOR I=NMAX TO NMIN                     ** Loop from max volume to min
1350   IF VEST(I)*SIGN>0 THEN GOTO 1450
1360     N=N+1                              ** Zero flow crossing
1370     SUMX=SUMX+MAX                      ** so MAX holds the maximum
1380     SUMXX=SUMXX+MAX*MAX                ** for the preceding vest
1390     SUMY=SUMY+PATIENT(I)               ** half cycle while PATIENT(I)
1400     SUMYY=SUMYY+PATIENT(I)*PATIENT(I)  ** hold the corresponding volume
1410     SUMXY=SUMXY+MAX*PATIENT(I)         ** Sum correlation values
1420     PRINT #1,PATIENT(I);",";MAX        ** Print to graphic file
1430     MAX=0
1440     SIGN=-SIGN                         ** Reinitialize
1450   IF ABS(VEST(I))<MAX THEN GOTO 1480
1460     MAX=ABS(VEST(I))                   ** New max vest induced flow
1470     NMAX=I                             ** and its position
1480 NEXT I
1490 CLOSE 1                                ** Close graphic file
1500 SUMXX=SUMXX-SUMX*SUMX/N
1510 SUMYY=SUMYY-SUMY*SUMY/N
1520 SUMXY=SUMXY-SUMX*SUMY/N
1530 R=SUMXY/SQR(SUMXX*SUMYY)               ** Correlation coefficient
1540 PRINT "R=";R;", N=";N;", MEAN=";SUMX/N ** MEAN= average peak flow
1550 RETURN

8000 REM - A TO D ROUTINE: UNIQUE TO EACH COMPUTER & CONVERTER BOARD
8500 RETURN

9000 CYCLES=INT(FREQ/2)                     ** Filter length about .5 second
9010 FLNG=INT(CYCLES*200/FREQ)+1            ** Filter length=integer # cycles
9020 MEAN=0
9030 BEGIN=FLNG-INT(FLNG/2)                 ** Beginning of filtered results
9040 FOR I=1 TO TLNG                        ** TLNG - total length
9050   PATIENT(I)=0
9060   J=INT(I-FLNG/2)                      ** Position of filtered results
9070   K=I-(FLNG-1)
9080   IF J<BEGIN THEN MEAN=MEAN+OBSERVE(I)    ** Accumulate for average
9090   IF J>=BEGIN THEN PATIENT(J)=MEAN/(FLNG-1) ** Compute average flow
9100   IF J>=BEGIN THEN MEAN=MEAN+FLOW(I)-FLOW(K) ** Move average 1 position
9110 NEXT I
9120 FINAL=TLNG-FLNG/2+1                    ** End of filtered results
9130 PATIENT(FINAL)=MEAN/(FLNG-1)
9140 RETURN
```

LINES 1005-1040 & 8000-8500: The 3 arrays are OBSERVE which holds the sampled, scaled results of the a-to-d conversion, PATIENT which first holds the flow signal generated by the patient and second the lung volume signal of the patient, and VEST which holds the flow induced by the vest system. The a-to-d conversion starts after the patient puts on the vest, the pump is set to 14 Hz, the patient is instructed to perform a maximum inspiration followed by a maximum expiration and the pump is started. The conversion is done at 200 Hz for 10 seconds to make sure the complete maneuver is captured. The zero flow value and the scale factors which convert the voltage values to flow in ml/sec have previously been found in the calibration stage and placed in a file for easy retrieval. Therefore the units of the values in OBSERVE are ml/sec. This routine has not been spelled out since it cannot be generalized to other systems.

LINES 1050-1060 & 9000-9140: The moving average filter is about 1/2 second long (FLNG) and is set to be an integer number of cycles in length, in this case it is derived from a frequency (FREQ) of 14 Hz. Since the moving average cannot generate the average until an FLNG number of points are available there are FLNG/2 number of points at the begin and the end of the array which are set to zero. TLNG, the total length, in this case is 2000. J is a pointer to the position for storing the average result while K is the position of the trailing filter point which is dropped after each average computation.

LINES 1070-1220: This loop finds the difference between the observed flow and the patient flow to get the vest induced flow and putting the result in VEST, computes the lung volume at each sample point by subtracting the flow divided by the sample frequency, stores these volume values back in PATIENT, and finds the points of maximum and minimum volume. The volumes, which start at 10000 and decrease as flow exits the lungs, are in ml units while the flows continue to be ml/sec.

LINES 1230-1490: The SIGN variable is used to keep track of whether the vest induced flows are greater than or less than zero. As soon as a zero crossing is detected this variable changes sign, the maximum flow and the lung volume at that point are printed out for future reference, the sums needed for the calculation of the correlation coefficient are accumulated, and MAX is reset to zero to begin the search for the next peak flow. This routine finds the absolute value of peak flow so both positive and negative peak flows are found, giving two such values per cycle.

LINES 1500-1550: The correlation coefficient R is computed using a standard statistical technique. A positive R close to 1 means the vest effectiveness goes down as lung volume goes down, therefor the vest is too loose. A negative R close to -1 means the vest effectiveness goes up as lung volume goes down, therefor the vest is too tight. If two vest fittings are to be compared which do not show a significant correlation between lung volume and vest effectiveness then the mean of the peak flows can be used. If a graphical representation of the data is preferred the file GRAPH.PLT can be used to generate it.

APPENDIX B   (VEST FREQUENCY TUNING ROUTINE)

```
3010 PRINT "SET FREQUENCY TO ";F(NXT)        ** Do analog to digital sampling
3020 TIME=2                                  ** for 2 seconds at 200 Hz and
3030 INPUT "PATIENT READY?";A$               ** put scaled values in OBSERVE
3040 GOSUB 8000
3050 REM - FILTER TO GET PATIENT FLOW
3060 FREQ=F(NXT)                             ** Moving average filter OBSERVE
3070 GOSUB 9000                              ** and put results in PATIENT
3080 REM - SEPARATE VEST FLOW
3090 FOR I=BEGIN TO FINAL
3100    VEST(I)=OBSERVE(I)-PATIENT(I)        ** Vest induced flow
3110 NEXT I
3120 REM - FIND PEAK VEST FLOWS & VEST PULSE VOLUMES
3130 SIGN=1                                  ** SIGN=1 when positive flow
3140 IF VEST(BEGIN)<0 THEN SIGN=-1           ** SIGN=-1 when negative
3150 N=0
3160 MAX=0
3170 VOL=0
3180 SUMX=0
3190 SUMY=0
3200 FOR I=BEGIN TO FINAL
3210    IF VEST(I)*SIGN>0 THEN GOTO 280
3220       N=N+1                             ** Zero flow crossing, MAX holds
3230       SUMX=SUMX+MAX                     ** peak flow of last vest half
3240       SUMY=SUMY+VOL                     ** cycle, VOL holds its volume
3250       MAX=0
3260       VOL=0
3270       SIGN=-SIGN                        ** Reinitialize
3280    VOL=VOL+ABS(VEST(I))/200             ** Integrate for volume (200 Hz)
3290    IF ABS(VEST(I))>MAX THEN MAX=ABS(VEST(I))  ** New peak vest flow
3300 NEXT I
3310 PEAK(NXT)=SUMX/N
3320 VVOL(NXT)=SUMY/N
3330 PRINT #1,F(NXT);",";VVOL(NXT);",";PEAK(NXT)
3340 PRINT "FREQUENCY=";F(NXT)
3350 PRINT "MEAN VEST INDUCED PEAK FLOW=";PEAK(NXT)
3360 PRINT "MEAN VEST INDUCED VOLUME=";VVOL(NXT)
3370 RETURN
```

LINES 3010-3040: The arrays contain the same values described in the vest fitting routine above except the PATIENT array is never updated to contain lung volumes. The frequency at which the pump is set is determined by the previous routine which determines in which order the frequencies should be used. Each frequency is displayed, the a-to-d conversion starts after the patient puts on the vest, the pump is set to the displayed frequency F(NXT), the patient is instructed to breath normally, and the pump is started. The conversion is done at 200 Hz for 2 seconds. The zero flow value and the scale factors which convert the voltage values to flow in ml/sec have previously been found in the calibration stage.

LINES 3050-3070: FREQ is set to the current frequency to be used. The rest of the moving average routine is exactly as described in the vest fitting routine, above.

LINES 3080-3110: Here the vest induced flow signal is separated from the OBSERVE array by subtracting the PATIENT flow signal.

LINES 3120-3280: SIGN again is used to keep track of whether the vest induced flow is positive or negative. During each half cycle of the vest induced flow signal the volume is computed and the peak flow is found. Each of these values are then summed.

LINES 3290-3350: The average peak flow and volume are computed. The current frequency and the corresponding peak flow and volume are saved to a file for later graphical output. These values are also printed for inspection.

APPENDIX C   (VEST FREQUENCY SELECTION ALGORITHM)

```
5010 FOR I=1 TO 17
5020    RANK(4,I)=1                                ** Frequency selection column
5030    RANK(2,I)=RANK(1,I)                        ** Poorest rank of column 1 & 3
5040    IF RANK(3,I)>RANK(1,I) THEN RANK(2,I)=RANK(3,I)
5050    RANK(2,I)=RANK(1,I)+RANK(3,I)+RANK(2,I)/100  ** Sum of 1 & 3 plus
5060 NEXT I                                           **    poorest/100
5070 FOR K=1 TO 2                                  ** Two best rankings
5080    FOR J=1 TO 3                               ** From each of the 3 columns
5090       MIN=4000                                ** Initialize search for best rank
5100       FOR I=1 TO 17                           ** Look at each frequency
5110          IF RANK(4,I)*RANK(J,I)>MIN THEN GOTO 5140
5120             MIN=RANK(4,I)*RANK(J,I)           ** New best unchosen rank found
5130             NMIN=I                            ** Position saved
5140       NEXT I
5150       RANK(4,NMIN)=100                        ** Frequency is marked as chosen
5160       N=(2-K)*3+J                             ** Second best are listed first
5170       CHOSE(N)=F(NMIN)                        ** Selected frequency saved
5180    NEXT J
5190 NEXT K
5200 FOR I=1 TO 6                                  ** Print frequency order
5210    PRINT "SELECTED FREQUENCY #";I;"=";CHOSE(I)
5220 NEXT I
5230 STOP
```

RANK is an array of 4 columns and 17 rows which correspond to the 17 frequencies (6-22) in the order presented for the testing sequence. The first column is the ranking from 1 to 17 of each of these frequencies with 1 giving the highest average peak flow and 17 giving the lowest. This sorting was done in the previous stage using a standard technique such as a shell or bubble sort. The third column contains the similar rankings for the average vest induced pulse volume. The second column is a non-parametric average ranking of these other two rankings. The fourth column keep track of which frequencies have already been selected during this process.

LINES 5010-5060: This loop sets up the rank array columns 2 and 4 for the selection process. The averaging of the ranking of peak flow and volume is created by adding the two rankings. If there is a tie between such rankings it is broken by looking at the poorest of the two rankings between the two tied frequencies. The one with the best of the poorest ranking is chosen (eg. 3+7=10 and 4+6=10 but 3+7+7/100=10.07 while 4+6+6/100=10.06 so the second one (10.06) is chosen).

LINES 5070-5190: The best peak flow is chosen first, then the best average ranking of peak flow and volume, and then the best volume. This is done again for the second best of these rankings. These rankings selections are ordered second best first and best second.

LINES 5200-5230: The frequency selections are displayed. Each frequency is to be used for 5 minutes during the expiration of deep breaths. The idea is to first give the chest a good thumping to loosen mucous, then increase the air volume moved slightly while still retaining some thumping action and finally supplying good air movement to move the mucous. This sequence is then repeated for the best frequencies for these functions.

What is claimed is:

1. Apparatus for optimizing fit and frequency of device which provides alternating compression to thoracic cavity of a person for purpose of enhancing respiration, said device including means for compressing said person's thoracic cavity, said compressing means being adjustable with respect to the thoracic cavity, said apparatus comprising:
   means for measuring actual air flow from said person during respiration while said alternating compression device is operating;
   means for computing from said measured actual air flow the parameters of normal air flow of said person as if said alternating compression device were not operating, normal lung volume of said person as if said alternating compression device were not operating, induced air flow peaks relative to said normal air flow and due to said alternating compression device operating, average of said induced air flow peaks, and average of induced changes in lung volume relative to said normal lung volume and due to said alternating compression device operating; and
   means for converting said measured actual air flow to an electrical signal compatible with said computing means;
   wherein the fit is optimized when said induced air flow peaks are substantially the same relative to normal lung volume during respiration and optimal frequencies occur when average induced air flow peaks and average induced lung volume changes are greatest.

2. A method for optimizing fit and frequency of device which provides alternating compression to thoracic cavity of a person for purpose of enhancing respiration, including means for compressing said person's thoracic cavity, means for measuring actual air flow from said person during respiration while said alternating compression device is operating, and means for computing various parameters from said actual air flow, said method comprising the steps of:
   installing said compressing means on said person;
   measuring observed air flow of said person during respiration to determine efficacy of said compressing means; and
   identifying alternating compression device frequencies which are optimal for enhancing said person's respiration.

3. The method in accordance with claim 2 wherein said measuring step includes the step of separating from said measured observed air flow said person's air flow due to respiration and induced air flow due to said compressing device and the step of relating said induced air flow to lung volume of said person.

4. The method in accordance with claim 3 wherein said relating step includes the step of identifying absolute values of induced peak air flow.

5. The method in accordance with claim 4 wherein said method includes the step of adjusting said compressing means until the absolute values of said induced peak air flow are substantially the same relative to lung volume during respiration.

6. The method in accordance with claim 2 wherein said frequency identifying step includes the steps of separating from said measured observed air flow said person's air flow due to respiration and induced air flow due to said compressing device, identifying absolute values of induced peak air flow, obtaining absolute values of integrated induced air flow over half cycle time periods to obtain induced changes in lung volume due to said alternating compression device.

7. The method in accordance with claim 6 wherein said frequency identifying step further includes the steps of averaging said absolute values of induced air flow peaks and said induced changes in lung volume over a selected time period, and ranking different frequencies in order from greatest to least for both absolute values of average induced peak flow and average induced changes in lung volume.

8. The method in accordance with claim 7 wherein said frequency identifying step also includes adding the two frequency rankings and reranking from lowest to highest with ties broken in favor of the frequency having the best of the poorest ranking of absolute values of average induced peak flow and average induced changes in lung volume.

9. The method in accordance with claim 8 wherein said frequency identifying step still further includes ordering frequencies as follows: second best absolute value of average induced peak flow, second best reranking, second best absolute value of average induced changes in lung volume, best value of average induced peak flow, best reranking, and best absolute value of average induced changes in lung volume.

* * * * *